US00PP20886P2

(12) United States Plant Patent
Hofmann

(10) Patent No.: US PP20,886 P2
(45) Date of Patent: Mar. 23, 2010

(54) *DIASCIA* PLANT NAMED 'INDIAIMPAB'

(50) Latin Name: *Diascia barberae*
Varietal Denomination: Indiaimpab

(75) Inventor: Silvia Hofmann, Mainz (DE)

(73) Assignee: InnovaPlant GmbH & Co. KG, Gensinger (DE)

( * ) Notice: Subject to any disclaimer, the term of this patent is extended or adjusted under 35 U.S.C. 154(b) by 0 days.

(21) Appl. No.: 12/291,556

(22) Filed: Nov. 12, 2008

(51) Int. Cl.
*A01H 5/00* (2006.01)

(52) U.S. Cl. ..... Plt./425

(58) Field of Classification Search ..... Plt./425
See application file for complete search history.

*Primary Examiner*—Annette H Para
(74) *Attorney, Agent, or Firm*—C. A. Whealy

(57) ABSTRACT

A new and distinct cultivar of *Diascia* plant named 'Indiaimpab', characterized by its compact and mounding plant habit; freely branching habit; dense and bushy growth habit; freely flowering habit; soft pink-colored flowers; and good garden performance.

1 Drawing Sheet

Botanical designation: *Diascia barberae.*
Cultivar denomination: 'Indiaimpab'.

BACKGROUND OF THE INVENTION

The present invention relates to a new and distinct cultivar of *Diascia* plant, botanically known as *Diascia barberae*, and hereinafter referred to by the name 'Indiaimpab'.

The new *Diascia* plant is a product of a planned breeding program conducted by the Inventor in Gensingen, Germany. The objective of the breeding program is to create new compact and freely branching *Diascia* cultivars with early flowering habit, large flowers, attractive flower colors and good garden performance.

The new *Diascia* plant originated from a cross-pollination made by the Inventor in Gensingen, Germany in July, 2003 of *Diascia barberae* 'Pendan', not patented, as the female, or seed, parent with a proprietary selection of *Diascia barberae* identified as code number D 04 14-3, not patented, as the male, or pollen, parent. The new *Diascia* was discovered and selected by the Inventor as a single flowering plant from within the progeny of the stated cross-pollination in a controlled greenhouse environment in Gensingen, Germany in May, 2004.

Asexual reproduction of the new *Diascia* plant by vegetative cuttings in a controlled greenhouse environment in Gensingen, Germany since May, 2004, has shown that the unique features of this new *Diascia* plant are stable and reproduced true to type in successive generations.

SUMMARY OF THE INVENTION

Plants of the new *Diascia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Indiaimpab'. These characteristics in combination distinguish 'Indiaimpab' as a new and distinct cultivar of *Diascia:*

1. Compact and mounding plant habit.
2. Freely branching habit; dense and bushy growth habit.
3. Freely flowering habit.
4. Soft pink-colored flowers.
5. Good garden performance.

Plants of the new *Diascia* can be compared to plants of the female parent, 'Pendan'. Plants of the new *Diascia* differ from plants of 'Pendan' in the following characteristics:

1. Plants of the new *Diascia* are more compact than plants of 'Pendan'.
2. Plants of the new *Diascia* are more freely branching and bushier than plants of 'Pendan'.
3. Plants of the new *Diascia* and 'Pendan' differ in flower color as plants of 'Pendan' have darker pink-colored flowers.

Plants of the new *Diascia* can be compared to plants of the male parent selection. Plants of the new *Diascia* differ from plants of the male parent selection in the following characteristics:

1. Plants of the new *Diascia* flower earlier than plants of the male parent selection.
2. Plants of the new *Diascia* and the male parent selection differ in flower color as plants of the male parent selection have apricot-colored flowers.

Plants of the new *Diascia* can be compared to plants of the *Diascia barberae* 'Diastara', disclosed in U.S. Plant Pat. No. 14,782. In side-by-side comparisons conducted in Gensingen, Germany, plants of the new *Diascia* differed from plants of 'Diastara' in the following characteristics:

1. Plants of the new *Diascia* were compact, denser and fuller than plants of 'Diastara'.
2. Plants of the new *Diascia* flowered more consistently under high temperature conditions than plants of 'Diastara'.

Plants of the new *Diascia* can also be compared to plants of the *Diascia barberae* 'Diastu', disclosed in U.S. Plant Pat. No. 13,949. In side-by-side comparisons conducted in Gensingen, Germany, plants of the new *Diascia* differed from plants of 'Diastu' in the following characteristics:

1. Plants of the new *Diascia* were compact, denser and fuller than plants of 'Diastu'.

2. Plants of the new *Diascia* were more mounding than plants of 'Diastu'.
3. Plants of the new *Diascia* had lighter pink-colored flowers than plants of 'Diastu'.

BRIEF DESCRIPTION OF THE PHOTOGRAPHS

The accompanying colored photographs illustrate the overall appearance of the new *Diascia*, showing the colors as true as it is reasonably possible to obtain in colored reproductions of this type. Colors in the photographs may differ slightly from the color values cited in the detailed botanical description which accurately describe the colors of the new *Diascia*.

The photograph at the bottom of the sheet is a side perspective view of a typical flowering plant of 'Indiaimpab' grown in a container.

The photograph at the top of the sheet is a close-up view of typical flowers, flower buds and leaves of 'Indiaimpab'.

DETAILED BOTANICAL DESCRIPTION

The aforementioned photographs and following observations, measurements and values describe plants grown in Bonsall, Calif. in 15-cm containers in an outdoor nursery during the summer and early fall under conditions which closely approximate commercial production. During the production of the plants, day temperatures ranged from 18° C. to 38° C. and night temperatures ranged from 10° C. to 24° C. Plants had been growing for seven weeks when the photographs and description were taken. In the description, color references are made to The Royal Horticultural Society Colour Chart, 2001 Edition, except where general terms of ordinary dictionary significance are used.

Botanical classification: *Diascia barberae* 'Indiaimpab'.

Parentage:

*Female, or seed, parent.*—*Diascia barberae* 'Pendan', not patented.

*Male or pollen parent.*—Proprietary selection of *Diascia barberae* identified as code number D 04 14-3, not patented.

Propagation:

*Type.*—By vegetative cuttings.

*Time to initiate roots, summer.*—About seven days at 24° C.

*Time to initiate roots, winter.*—About eight to nine days at 21° C.

*Time to produce a rooted young plant, summer.*—About 28 days at 24° C.

*Time to produce a rooted young plant, winter.*—About 30 days at 21° C.

*Root description.*—Fibrous, fine; white in color.

*Rooting habit.*—Freely branching; moderately dense.

Plant description:

*Plant form and growth habit.*—Compact and mounding plant habit; vigorous growth habit.

*Branching habit.*—Freely branching habit; dense and bushy growth habit; about twelve primary lateral branches each with potentially two secondary laterals developing at every node.

*Plant height.*—About 15 cm.

*Plant diameter* (*area of spread*).—About 36 cm.

Lateral branch description:

*Length.*—About 16.5 cm.

*Diameter.*—About 2 mm.

*Internode length.*—About 2 cm.

*Texture.*—Smooth, glabrous.

*Color.*—Close to 145A.

Foliage description:

*Arrangement.*—Opposite, simple.

*Length.*—About 2 cm.

*Width.*—About 1.6 cm.

*Shape.*—Elliptical to cordate.

*Apex.*—Acute, cuspidate.

*Base.*—Slightly cordate.

*Margin.*—Serrate.

*Texture, upper and lower surfaces.*—Smooth, glabrous.

*Venation pattern.*—Pinnate; arcuate.

*Color.*—Developing leaves, upper surface: Close to N137C. Developing leaves, lower surface: Close to 147B. Fully expanded leaves, upper surface: Close to 137A; venation, close to 137A. Fully expanded leaves, lower surface: Close to 147B; venation, close to 147C.

*Petiole.*—Length: About 3 mm. Diameter: About 1.5 mm. Texture, upper and lower surfaces: Smooth, glabrous. Color, upper and lower surfaces: Close to 138A.

Flower description:

*Flower arrangement.*—Single flowers arranged on terminal racemes; flowers zygomorphic with five lobes fused at the base and twin-spurred. Freely flowering habit with usually about 32 to 34 open flowers and flower buds per raceme. Flowers face upright and outwardly.

*Fragrance.*—None detected.

*Natural flowering season.*—Plants flower freely and continuously from the spring into the fall in Southern California.

*Flower longevity.*—Flowers last about two to three days on the plant; flowers not persistent.

*Inflorescence height.*—About 6.7 cm.

*Inflorescence diameter.*—About 4 cm.

*Flower diameter.*—About 1.5 cm.

*Flower height.*—About 1.7 cm.

*Flower depth.*—About 9 mm.

*Flower bud.*—Length: About 5 mm. Diameter: About 7 mm. Shape: Round to oval. Color: Close to 186A to 186B.

*Corolla.*—Arrangement: Corolla consists of five petals modified into two banner petals, two lateral petals with spurs and a protruding lower lip petal. Banner lobe length: About 4 mm. Banner lobe width: About 5 mm. Lateral lobe length: About 6 mm. Lateral lobe width: About 7 mm. Lower lobe length: About 9 mm. Lower lobe width: About 1.2 cm. Banner, lateral and lower lobe shape: Orbicular, rounded. Banner, lateral and lower lobe apex: Rounded. Banner, lateral and lower lobe margin: Entire. Banner, lateral and lower lobe texture, upper and lower surfaces: Smooth, glabrous; velvety. Spur length: About 4 mm. Spur diameter: About 2 mm. Spur orientation: Curved downward. Color, banner petals: When opening, upper surface: Close to 69B. When opening, lower surface: Close to 186B to 186C. Fully developed, upper surface: Close to 69B to 69C; color becoming closer to 76D with development; towards the base of the banner lobes, eyespot, close to 13B. Fully developed, lower surface: Close to 75C to 75D. Corolla tube, inside: Close to 60C to 60D. Color, lateral petals: When opening, upper surface: Close to 69B. When opening, lower surface: Close to 186B to 186C. Fully developed, upper surface: Close to 69B to 69C; color becoming closer to 76D with development; towards the base of the lateral lobes, small spots, close to 64B. Fully developed, lower surface: Close to 75A; color becoming closer to N77D with development; spurs, close to N77D. Color, lower petal: When opening, upper surface: Close to 69B. When opening, lower surface: Close to 186B to 186C. Fully developed, upper surface: Close to 69B to 69C; color becoming closer to 76D with development. Fully developed, lower surface: Close to 69C.

*Sepals.*—Appearance: Five sepals fused into a star-shaped calyx. Length: About 2 mm. Width: About 1.5 mm. Shape: Elliptical. Apex: Acute. Margin: Entire. Texture, upper surface: Smooth, glabrous. Texture, lower surface: Pubescent. Color, upper and lower surfaces: Close to 138A.

*Peduncles.*—Length: About 2.3 cm. Diameter: About 1.5 mm. Texture: Sparsely pubescent. Color: Close to 144A.

*Pedicels.*—Length: About 1 cm. Diameter: Less than 1 mm. Texture: Sparsely pubescent. Color: Close to 144A.

*Reproductive organs.*—Androecium: Stamen number per flower: About four. Filament length: About 2 mm. Filament color: Close to 186C. Anther shape: Ovoid. Anther length: About 1 mm. Anther color: Close to 10A. Amount of pollen: Scarce. Pollen color: Close to 10A. Gynoecium: Pistil number per flower: One. Pistil length: About 4 mm. Style length: About 1 mm. Style color: Close to 145A. Stigma color: Close to 151B. Ovary color: Close to 144B.

*Seed/fruit.*—Seed and fruit production have not been observed.

Garden performance: Plants of the new *Diascia* have been observed to have good garden performance and tolerate rain, wind and temperatures ranging from about 12° C. to about 40° C.

Pathogen/pest resistance: Plants of the new *Diascia* have not been shown to be resistant to pathogens and pests common to *Diascia*.

It is claimed:

1. A new and distinct *Diascia* plant named 'Indiaimpab' as illustrated and described.

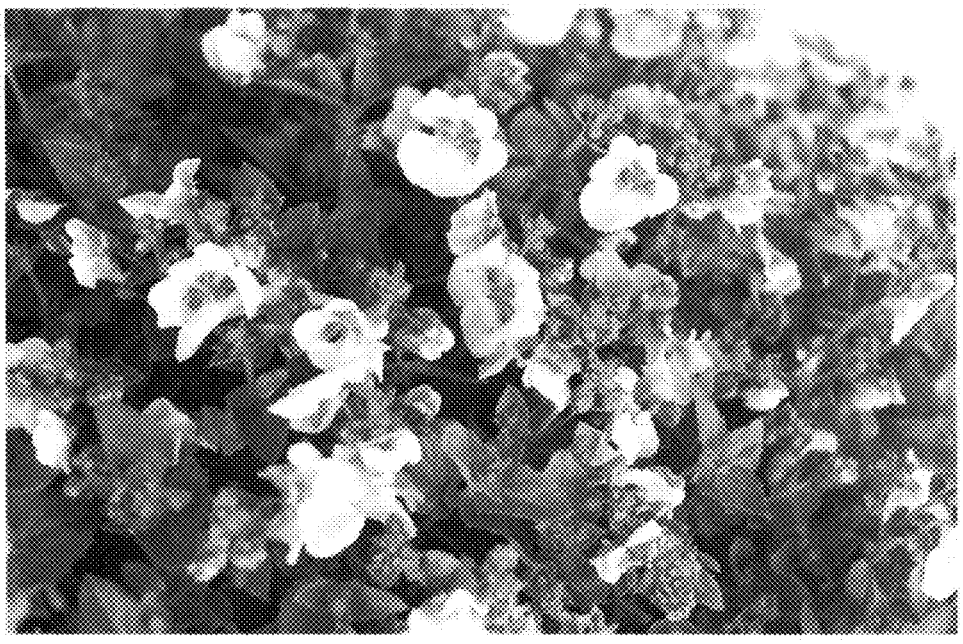
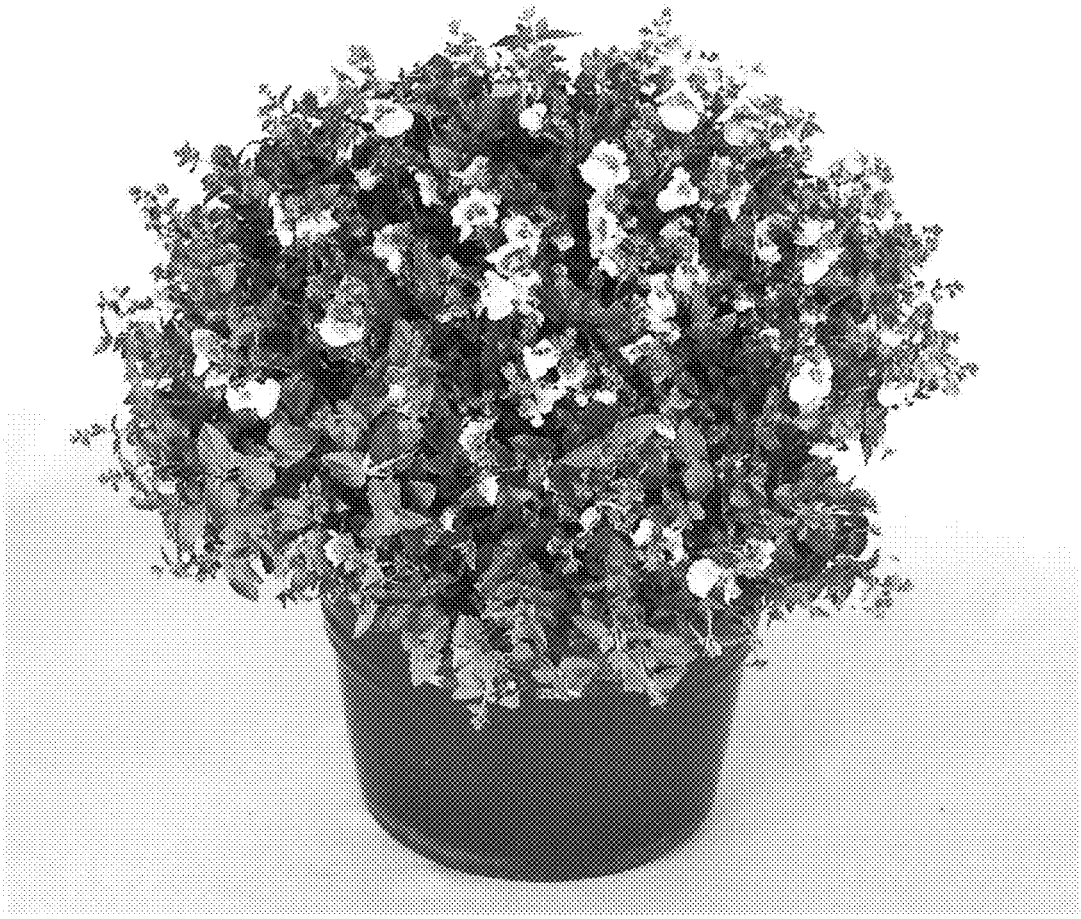

* * * * *